(12) United States Patent
MacTaggart et al.

(10) Patent No.: US 12,178,465 B2
(45) Date of Patent: *Dec. 31, 2024

(54) SURGICAL DEVICES AND METHODS

(71) Applicant: Board of Regents of the University of Nebraska, Lincoln, NE (US)

(72) Inventors: Jason N. MacTaggart, Omaha, NE (US); Alexey Kamenskiy, Omaha, NE (US); Paul Deegan, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/379,748

(22) Filed: Oct. 13, 2023

(65) Prior Publication Data

US 2024/0108376 A1  Apr. 4, 2024

Related U.S. Application Data

(63) Continuation of application No. 17/469,550, filed on Sep. 8, 2021, now Pat. No. 11,806,040, which is a continuation of application No. 16/618,833, filed as application No. PCT/US2018/037334 on Jun. 13, 2018, now Pat. No. 11,116,537.

(Continued)

(51) Int. Cl.
| | |
|---|---|
| *A61B 17/3203* | (2006.01) |
| *A61F 2/07* | (2013.01) |
| *A61B 17/00* | (2006.01) |
| *A61B 17/32* | (2006.01) |

(Continued)

(52) U.S. Cl.
CPC .......... *A61B 17/32037* (2013.01); *A61F 2/07* (2013.01); *A61B 2017/00473* (2013.01); *A61B 2017/320052* (2013.01); *A61B 2217/005* (2013.01); *A61F 2002/9528* (2013.01); *A61M 25/09* (2013.01)

(58) Field of Classification Search
CPC .......... A61B 17/3203; A61B 17/32037; A61B 2017/00473; A61B 2017/320052; A61B 2217/005; A61F 2/07; A61F 2002/9528
See application file for complete search history.

(56) References Cited

U.S. PATENT DOCUMENTS

| | | |
|---|---|---|
| 5,496,267 A | 3/1996 | Drasler et al. |
| 5,527,330 A | 6/1996 | Tovey |

(Continued)

OTHER PUBLICATIONS

International Preliminary Report on Patentability in International Appln. No. PCT/US2018/037334, dated Aug. 9, 2018, 6 pages.

(Continued)

*Primary Examiner* — Ryan J. Severson
(74) *Attorney, Agent, or Firm* — Fish & Richardson P.C.

(57) ABSTRACT

An intravascular cutting device described herein uses high-pressure water, saline, or other fluid to cut tissue and other materials including but not limited to calcified tissue, stents, stent grafts, and other devices. In some embodiments, the cutting device includes a working end that has a nozzle with a hole to allow the release of a high-pressure fluid jet. Opposite of the nozzle is a catch plate or deflector anvil that prevents the fluid jet from cutting healthy tissue. The device user will place the item to be cut between the nozzle and catch plate and then advance the device along the item to be cut as the fluid jet is activated, thus cutting the object as it advances.

20 Claims, 10 Drawing Sheets

Related U.S. Application Data

(60) Provisional application No. 62/518,656, filed on Jun. 13, 2017.

(51) Int. Cl.
*A61F 2/95* (2013.01)
*A61M 25/09* (2006.01)

(56) References Cited

U.S. PATENT DOCUMENTS

| | | |
|---|---|---|
| 6,129,697 A | 10/2000 | Drasler et al. |
| 6,375,635 B1 | 4/2002 | Moutafis et al. |
| 6,960,182 B2 | 11/2005 | Moutafis et al. |
| 6,984,239 B1 | 1/2006 | Drasler et al. |
| 7,122,017 B2 | 10/2006 | Moutafis et al. |
| 8,062,246 B2 | 11/2011 | Moutafis et al. |
| 9,782,195 B2 | 10/2017 | Mactaggart et al. |
| 10,779,851 B2 | 9/2020 | Mactaggart et al. |
| 10,932,810 B2 | 3/2021 | Malhi et al. |
| 11,116,537 B2 | 9/2021 | Mactaggart et al. |
| 2002/0111579 A1 | 8/2002 | Moutafis et al. |
| 2002/0177802 A1 | 11/2002 | Moutafis et al. |
| 2005/0159765 A1 | 7/2005 | Moutafis et al. |
| 2006/0100569 A1 | 5/2006 | McRury et al. |
| 2006/0129086 A1 | 6/2006 | McRury et al. |
| 2006/0229550 A1 | 10/2006 | Staid et al. |
| 2010/0228273 A1 | 9/2010 | Staid et al. |
| 2015/0142030 A1 | 5/2015 | Mactaggart et al. |
| 2018/0042630 A1 | 2/2018 | Mactaggart et al. |
| 2020/0129201 A1 | 4/2020 | MacTaggart et al. |
| 2021/0401452 A1 | 12/2021 | MacTaggart et al. |

OTHER PUBLICATIONS

International Search Report and Written Opinion in Appln. No. PCT/US2018/37334, dated Aug. 30, 2018, 7 pages.

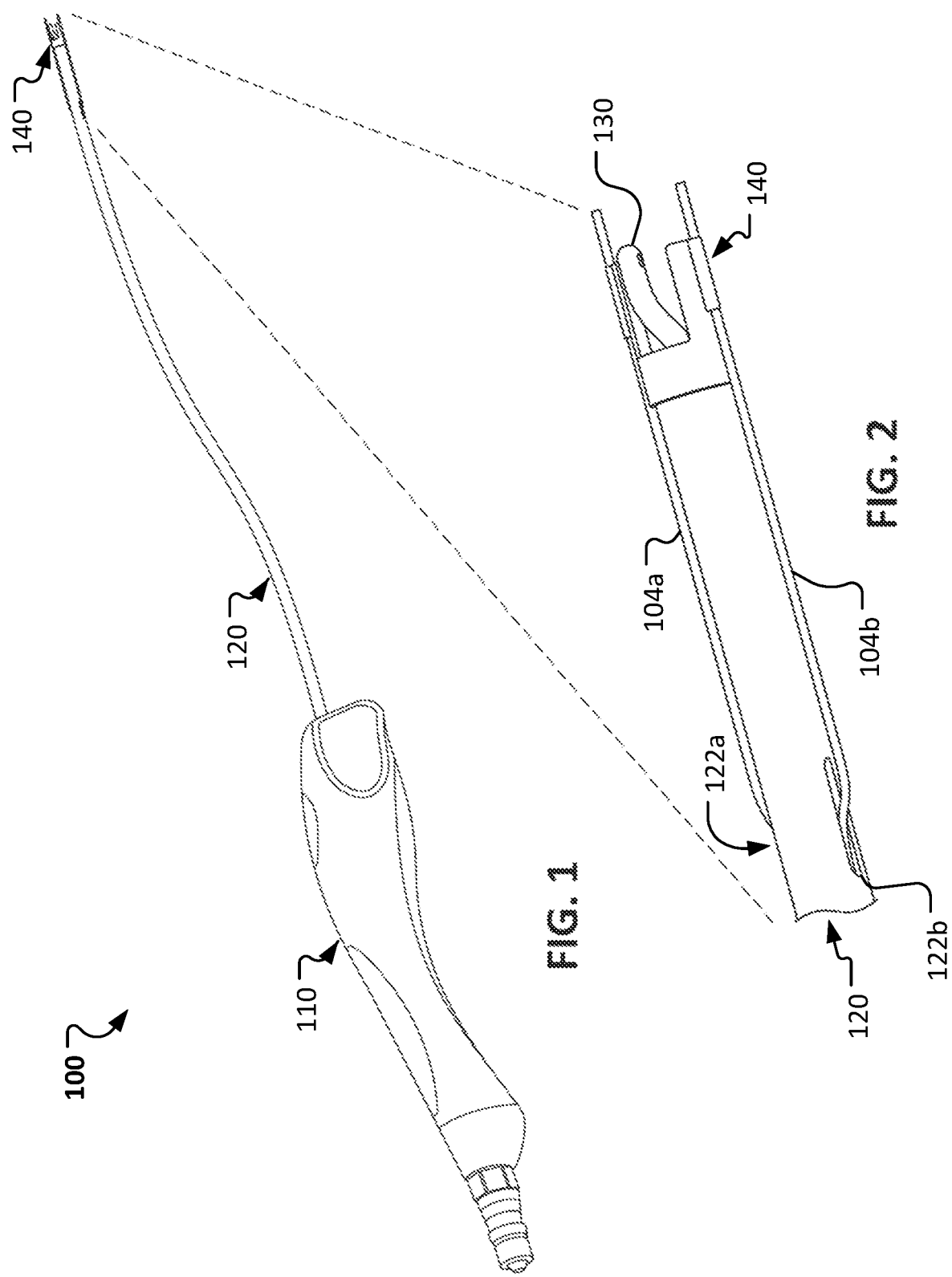

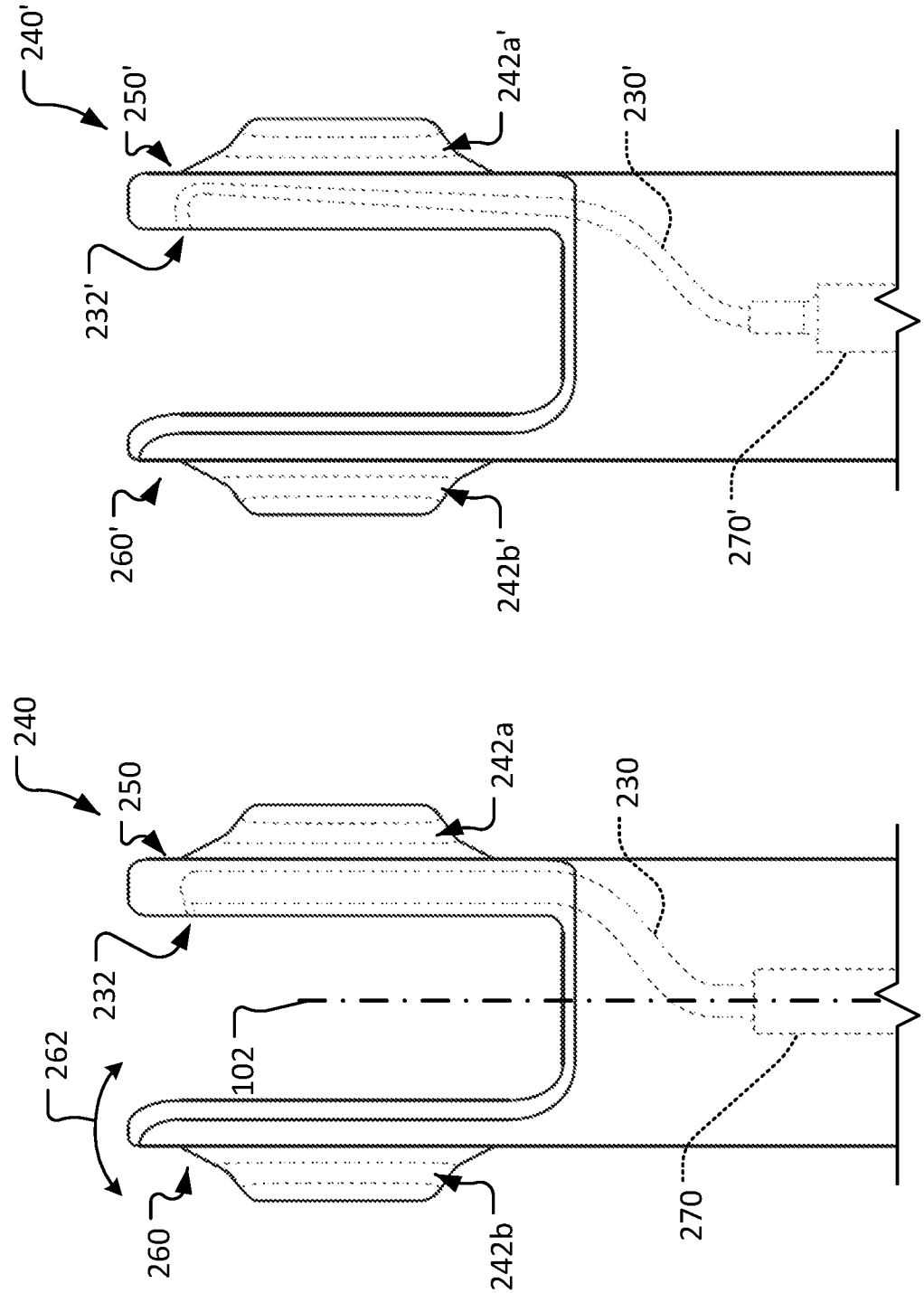

SURGICAL DEVICES AND METHODS

CROSS REFERENCE TO RELATED APPLICATION

This application is a continuation of U.S. application Ser. No. 17/469,550, filed on Sep. 8, 2021, which is a continuation of U.S. application Ser. No. 16/618,833, filed on Dec. 3, 2019 (now U.S. Pat. No. 11,116,537), which is a National Stage Application under 35 U.S.C. § 371 of International Application No. PCT/US2018/037334, filed on Jun. 13, 2018, which claims the benefit of U.S. Provisional Application Ser. No. 62/518,656, filed Jun. 13, 2017. The disclosure of the prior applications are considered part of (and are incorporated by reference in) the disclosure of this application.

BACKGROUND

1. Technical Field

This document relates to devices and methods for intravascular modifications. For example, this document relates to intravascular cutting devices that use high-pressure water, saline, or other fluid to cut tissue and other materials including but not limited to calcified tissue, stents, stent grafts, and other devices.

2. Background Information

Arterial dissection is a deadly disease caused by a tear in the tunica intima of an artery, forming a false lumen. A thin wall or septum resulting from the tear creates a double barrel portion of the artery, with blood flow on both sides of the septum. The false lumen is on one side of the septum while the true lumen is on the other side. Some arterial dissections can extend up to a meter in length. If untreated, death from rupture or downstream organ ischemia can occur. For patients that survive the initial episode, a chronic dissection occurs and often progresses to an aneurysm with significant aortic rupture risk.

The main surgical method for arterial dissection reconstruction involves open surgical exposure of the artery and associated branch vessels, clamping of the arteries, and then cutting through all three layers of the artery in order to access and repair the dissection. Often the surgeon adds a prosthetic graft to repair the artery wall and re-establish arterial continuity. Clamping arteries and cutting through healthy tissues to repair aortic dissections causes undesired consequences of extra stress placed on the heart with clamping, downstream organ dysfunction from lack of blood flow during clamping, and healthy tissue injury, such as nerve and lung injuries from surgical exposures. Sometimes septum fenestration, or creating a cut in the septum to connect the true and false lumens, is performed to relieve downstream organ ischemia.

A stent is a mesh, tube-like structure often used in conjunction with angioplasty to permanently hold open an artery, allowing for unrestricted blood flow, or to support a weakness in the artery wall called an aneurysm. In some cases, the artery reacts to the stent (e.g., perceives it as a foreign body) and responds by mounting an immune system response which leads to further narrowing near or inside the stent. Restenosis is the recurrence of stenosis, a narrowing of a blood vessel, leading to restricted blood flow. Restenosis usually pertains to an artery or other large blood vessel that has become narrowed, received treatment to clear the blockage and subsequently become re-narrowed. Rates of restenosis differ between devices (e.g., stent-grafts, balloon angioplasty, etc.) and location of procedure (i.e., centrally located in the heart, such as the coronary artery, or in peripheral vessels such as the popliteal artery in the leg, the pudendal artery in the pelvis, or the carotid artery in the neck). A 2003 study of selective and systematic stenting for limb-threatening ischemia reported restenosis rates at one-year follow-up in 32.3% of selective stenting patients and 34.7% of systematic stenting patients.

SUMMARY

This document describes devices and methods for intravascular modifications. For example, this document describes intravascular cutting devices that use high-pressure water, saline, or other fluids to cut tissue and other materials including but not limited to calcified tissue, stents, stent grafts, valves, occluders, screws, implants, and other devices. In some embodiments, the cutting device includes a working end that has a nozzle with a hole to allow the release of a high-pressure fluid jet. Opposite of the nozzle is a catch plate or deflector anvil that prevents the fluid jet from cutting healthy tissue. The device user will place the item to be cut between the nozzle and catch plate and then advance the device along the item to be cut as the fluid jet is activated, thus cutting the material as it advances.

In one aspect, this disclosure is directed to an intravascular cutting device that includes a handle, a catheter extending distally from the handle, and a cutting head extending distally from a distal end of the catheter. In some embodiments, the catheter defines a first guidewire lumen and a second guidewire lumen. The first and second guidewire lumens extend along the catheter and distally terminate at respective locations through outer diameter wall surface of the catheter. The respective locations can be proximal of a distal end of the catheter. The catheter can include a hypotube defining a cutting fluid conveyance lumen. The cutting head, extending distally from the distal end of the catheter, defines a first cutting head guidewire lumen and a second cutting head guidewire lumen. The cutting head can include a fluid jet prong defining a cutting head lumen in fluid communication with the cutting fluid conveyance lumen. The cutting head lumen distally terminates at a nozzle opening. The cutting head can also include a deflector prong defining a cutting fluid deflection surface facing toward the nozzle opening such that cutting fluid emitted from the nozzle opening strikes the cutting fluid deflection surface.

Such an intravascular cutting device can optionally include one or more of the following features. The cutting head can be selectively attachable and detachable from the catheter by a user of the intravascular cutting device. The cutting head can be a first cutting head, and the intravascular cutting device can also include a second cutting head that selectively attachable and detachable from the catheter by a user of the intravascular cutting device. In some embodiments, the first cutting head guidewire lumen is radially aligned with the fluid jet prong and/or the second cutting head guidewire lumen is radially aligned with the deflector prong. In some embodiments, the first cutting head guidewire lumen is not radially aligned with the fluid jet prong and/or the second cutting head guidewire lumen is not radially aligned with the deflector prong. In particular embodiments, the first cutting head guidewire lumen is radially outward of the fluid jet prong and/or the second cutting head guidewire lumen is radially outward of the deflector prong. In some example embodiments, the first cutting head guidewire lumen is radially inward of the fluid jet prong and the second cutting head guidewire lumen is radially inward of the deflector prong. The fluid jet prong may comprise the hypotube of the catheter such that the cutting head lumen is defined by the hypotube. In some embodiments, the hypotube of the catheter distally terminates proximal of the fluid jet prong. In particular embodiments of the intravascular cutting device, the cutting head defines an aspiration lumen that distally terminates between the fluid jet prong and the deflector prong. The fluid jet prong may be pivotable in relation to the deflector prong and/or the deflector prong may be pivotable in relation to the fluid jet prong, such that a separation distance between respective distal ends of the fluid jet prong and the deflector prong is variable. In some embodiments, the hypotube of the catheter is a first hypotube and the cutting fluid conveyance lumen of the cutting head is a first cutting fluid conveyance lumen. In some such embodiments, the catheter also includes a second hypotube defining a second cutting fluid conveyance lumen, and both of the first and second cutting fluid conveyance lumens are in fluid communication with the cutting head lumen. Using such an arrangement, two cutting mediums can be mixed. For example, a suspended particulate matter can be mixed with a liquid to enhance the cutting performance of the fluid jet. In some embodiments, the intravascular cutting device also includes a valve arranged for selectively adjusting a mix ratio of fluids in the first and second cutting fluid conveyance lumens.

In another aspect, this disclosure is directed to a method of cutting a material within a circulatory system of a patient. The method can include one or all of the following steps: deploying a first guidewire within the circulatory system; deploying a second guidewire within the circulatory system and along an opposite side of the material in relation to the first guidewire; advancing any embodiment of the intravascular cutting devices described herein over the first and second guidewires such that the first guidewire is slidably disposed within: (i) the first guidewire lumen and (ii) the first cutting head guidewire lumen, and such that the second guidewire is slidably disposed within: (i) the second guidewire lumen and (ii) the second cutting head guidewire lumen; and supplying a cutting fluid into the cutting fluid conveyance lumen while the fluid jet prong and the deflector prong are on opposite sides of the material such that the cutting fluid: (i) sprays out of the nozzle opening, (ii) cuts through the material, and (iii) strikes the cutting fluid deflection surface.

Such a method of cutting a material within a circulatory system of a patient may optionally include one or more of the following features. During the advancing, the first and second guidewires may each extend along an exterior of the catheter between: (i) the respective locations through the outer diameter wall surface of the catheter and (ii) the first and second cutting head guidewire lumens. The material being cut may be a soft tissue, a fabric of an implantable prosthetic device, a metal framework of an implantable prosthetic device, and/or any other type of material without limitation. The method of cutting a material within a circulatory system of a patient may also include aspirating the cutting fluid and particles of the material from between the fluid jet prong and the deflector prong while supplying the cutting fluid.

In another aspect, this disclosure is directed to a method of cutting a stent located within a vessel of a patient. The method can include one or all of the following steps: deploying a first guidewire through a lumen of the stent; deploying a second guidewire exteriorly along the stent either within a wall of the vessel or outside of the vessel; deploying a stent graft within the lumen of the stent; advancing any embodiment of the intravascular cutting devices described herein over the first and second guidewires such that the first guidewire is slidably disposed within: (i) the first guidewire lumen and (ii) the first cutting head guidewire lumen, and such that the second guidewire is slidably disposed within: (i) the second guidewire lumen and (ii) the second cutting head guidewire lumen; and supplying a cutting fluid into the cutting fluid conveyance lumen while the fluid jet prong and the deflector prong are on opposite sides of the stent such that the cutting fluid: (i) sprays out of the nozzle opening, (ii) cuts through the stent, and (iii) strikes the cutting fluid deflection surface.

Such a method of cutting a stent located within a vessel of a patient may optionally include one or more of the following features. The cutting fluid may include particulate matter. The method may also include aspirating the cutting fluid and particles of the stent from between the fluid jet prong and the deflector prong while supplying the cutting fluid.

Particular embodiments of the subject matter described in this document can be implemented to realize one or more of the following advantages. In some embodiments, conditions such as, but not limited to, arterial dissections and others can be treated using the devices and methods provided herein. In some embodiments, the devices and methods described herein can be advantageously used to cut tough materials within the body of a patient. Such materials can include, but are not limited to, calcified lesions, metallic stents, metallic and fabric stent grafts, plastics, materials of prosthetic valves and other implantable prosthetic devices, bone screws, and other materials. In some embodiments, aspiration is used to mitigate creation of emboli. In some embodiments, various conditions can be treated in a minimally invasive fashion using the devices and methods provided herein. In comparison to more invasive surgical approaches, such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1 is a perspective view of an example intravascular cutting device in accordance with some embodiments provided herein.

FIG. 2 is a perspective view of an example distal tip portion of the intravascular cutting device of FIG. 1.

FIG. 7 is side view of another example cutting head that can be included in some embodiments of the intravascular cutting devices described herein.

FIG. 8 is side view of another example cutting head that can be included in some embodiments of the intravascular cutting devices described herein.

Like reference numbers represent corresponding parts throughout.

DETAILED DESCRIPTION

Figure 4:
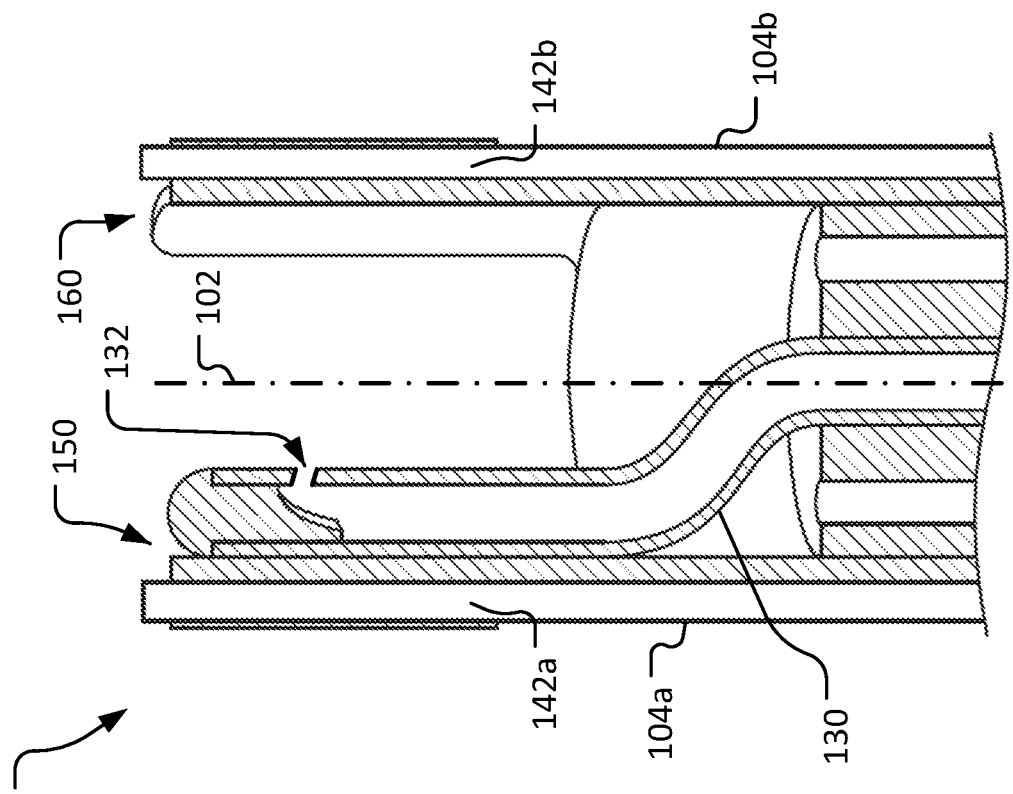
FIG. 4 is a longitudinal cross-sectional view of the cutting head of FIG. 3.

This document describes devices and methods for intravascular modifications. For example, this document describes intravascular cutting devices that use high-pressure water, saline, or other fluids to cut tissue and other materials including but not limited to calcified tissue, stents, stent grafts, valves, occluders, screws, implants, and other devices. In some embodiments, the cutting device includes a working end that has a nozzle with a hole to allow the release of a high-pressure fluid jet. Opposite of the nozzle is a catch plate or deflector anvil that prevents the fluid jet from cutting healthy tissue. The device user will place the item to be cut between the nozzle and catch plate and then advance the device along the item to be cut as the fluid jet is activated, thus cutting the material as it advances.

Within the nozzle is a fluid tube (which may be a hypotube) that conveys fluid from a pump. The fluid tube may be made of a variety of materials including plastic, metal, plastic reinforced with metal braiding, etc. The fluid tube can be a variety of diameters. In general, the internal diameter of the fluid tube is between 0.001" and 0.100" (0.0254 mm and 2.54 mm). In another embodiment, the internal diameter of the fluid tube is between 0.02" and 0.05" (0.508 mm and 1.27 mm). In one embodiment, the internal diameter of the fluid tube is about 0.024" (0.6096 mm). The internal fluid tube may also taper at various point with in the device. So, in some areas the fluid tube may have a wider internal diameter and at other points it may have a narrower internal diameter. The fluid tube may be in a straight line from the pump to the tip of the nozzle. Alternatively, the fluid tube may have bends or curves in it between the pump and the tip of the nozzle.

The nozzle contains a small hole that will allow the fluid jet to exit the device and cut tissue or other materials. The fluid jet nozzle hole diameter may range from 0.001" to 0.020" (0.0254 mm and 0.508 mm). In one embodiment the fluid jet nozzle hole diameter is between 0.002" and 0.006" (0.0508 mm and 0.1524 mm). In another embodiment the fluid jet nozzle hole diameter is between 0.003" and 0.005" (0.0762 mm and 0.127 mm). The fluid jet hole may be positioned within the nozzle so that the fluid jet is emitted straight out of the nozzle and towards the catch plate. Alternatively the fluid jet nozzle hole may be positioned within the nozzle so that the fluid jet is emitted at an angle towards the catch plate (e.g., the fluid jet is emitted at a slight downward angle into the catch plate). In some embodiments, the angle may be between 1° and 40°. In another embodiment, the angle may be between 10° and 30°. The nozzle may also contain a notch around the fluid jet nozzle hole. The nozzle may sit next to a back plate. This back plate can be used to connect guidewires to the device.

The catch plate can be made of a variety of materials including but not limited to metals and plastics. The catch plate can be curved or straight. The catch plate can have a variety of widths. In one embodiment, the catch plate takes up between 10% to 80% of the circumference of the tip of the device. In another embodiment, the catch plate takes up between 20% to 60% of the circumference of the tip of the device. In another embodiment, the catch plate takes up between 20% to 50% of the circumference of the tip of the device. In one embodiment, the catch plate sits around the catheter portion of the device.

The device may be packaged within a catheter. The catheter can be made from a variety of materials including but not limited to plastics such as thermoplastic elastomers (e.g., Pebax®). The catheter may have multiple lumens. The fluid tube will be contained within the catheter. Other components such as suction and imaging devices can be packaged within the catheter. The catheter may also contain guidewires.

The device may use guidewires. The guidewires may be contained fully within the catheter or the guidewires may sit outside of the catheter, or the guidewires may sit outside of one section of the catheter and be contained within the catheter in another section. In one embodiment the guidewires exit the catheter, run along the outside of the catheter, and are attached to the back side (outside) of the catch plate and the back side (outside) of the back plate that is next to the nozzle.

The device of the present invention can be used to treat diseases/disorders. In one embodiment the device is used to cut tissue septa. In one embodiment the tissue septum is due to an arterial or venous dissection. In one embodiment the dissection includes but is not limited to an aortic dissection, a carotid artery dissection, a vertebral artery dissection, and coronary artery dissection. The device of the present invention may also be used to cut non-biological materials including but not limited to stents, stent grafts, catheters etc.

Additional component descriptions and methods of use are described in U.S. patent application Ser. No. 14/548,046 filed on Nov. 19, 2014, incorporated by reference herein in its entirety.

Referring to FIG. 1, an example intravascular cutting device 100, in accordance with some embodiments provided herein, can be used to cut tissue and other materials including but not limited to calcified tissue, bone, stents, stent grafts, and other materials and devices within the body of a patient in a minimally invasive manner. As described further herein, the intravascular cutting device 100 can be configured in many different arrangements, can include one or more various optional features, and can be used in many different manners. All possible combinations and permutations of arrangements, features, and uses are within the scope of this disclosure. Moreover, the descriptions provided herein are not to be construed as limiting, and one of ordinary skill in the art will readily envision and comprehend additional analogous arrangements, features, and uses of the intravascular cutting device 100 beyond those expressly described herein, which are also within the scope of this disclosure.

The example intravascular cutting device 100 broadly includes a handle 110, a catheter 120, and a cutting head 140. The catheter 120 is attached to, and extends distally from, the handle 110. The cutting head 140 is attached to, and extends distally from, a distal end portion of the catheter 120. In some embodiments, the cutting head 140 is selectively attachable and detachable from the catheter 120 such that a clinician user can select different types or sizes of cutting heads for different purposes.

Figure 9:
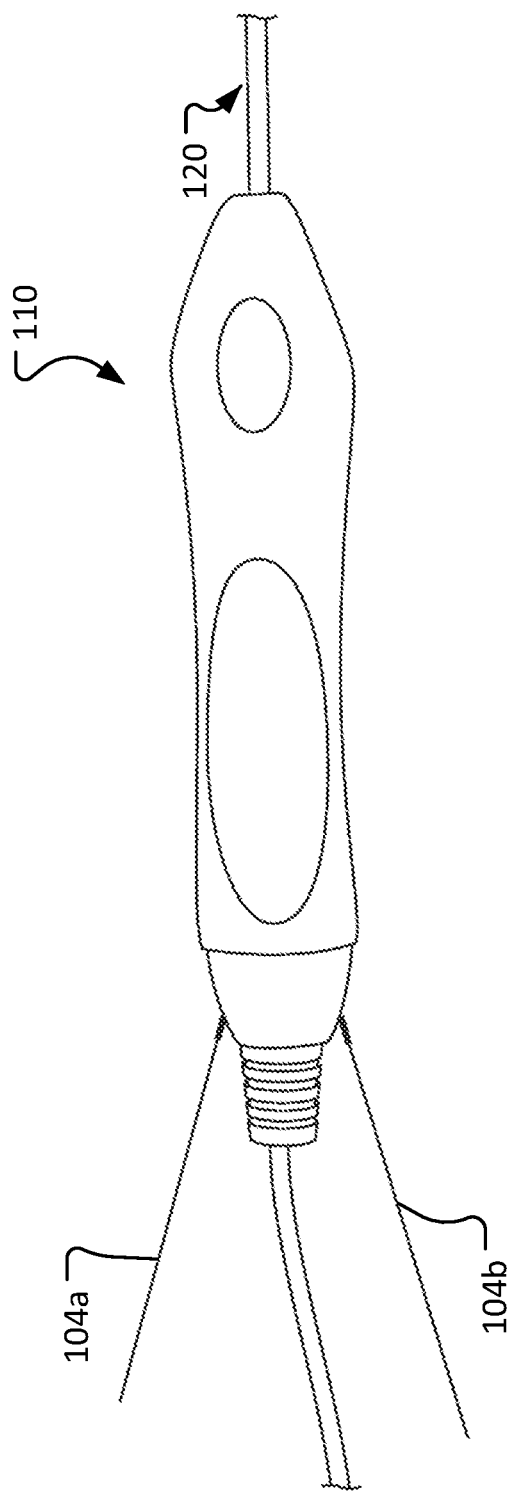
FIG. 9 shows an example handle portion of the intravascular cutting device of FIG. 1.

The handle 110 can be connected to various other supportive devices/systems. For example, in some cases one or more pumps can be connected to the handle 110. Such one or more pumps can serve as a supply of pressurized cutting fluids. In some cases, a source of vacuum can be connected to the handle 110. Such a vacuum source can provide suction for aspiration at the cutting head 140. In some cases, the handle 110 includes one or more actuators or control mechanisms. For example, the handle 110 can include a trigger, button, tab, lever, knob or other type of actuator that can be used by a clinician to start and/or stop a supply flow of cutting fluid to the cutting head 140. In some embodiments, the handle 110 can include a trigger, button, tab, lever, knob, or other type of actuator that can be used by a clinician to start and/or stop suction for aspiration at the cutting head 140. In particular embodiments, one or more portions of the catheter 120 can be selectively deflectable for steering purposes and the user-controls for the deflection can be located at/on the handle 110. In some embodiments (e.g., as shown in FIG. 9), one or more guidewires 104*a* and 104*b* enter/exit from ports of the handle 110, and slidably pass through lumens defined within the handle 110.

The example intravascular cutting device 100 also includes the catheter 120 that is attached to, and extends distally from, the handle 110. The catheter 120 terminates at a distal end portion, to which the cutting head 140 is attached. The catheter 120 can be laterally flexible/compliant while being sufficiently kink resistant. In some embodiments, the catheter 120 can be used within a working channel of an endoscope or laparoscope. In some embodiments, the catheter 120 can be adapted to be used in conjunction with a tele-operated surgical system ("robotic" surgical system).

The catheter 120 can be made of any suitable material and combinations of materials. For example, in some embodiments the catheter 120 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the catheter 120 can be made from metallic materials such as, but not limited to, nitinol, stainless steel, stainless steel alloys, titanium, titanium alloys, and the like, and combinations thereof. In some embodiments, the catheter 120 can be made from combinations of such polymeric and metallic materials (e.g., polymer layers with metal braid, coil reinforcement, stiffening members, and the like, and combinations thereof). Some portions of the catheter 120 can be constructed differently from other portions of the catheter 120. For example, in some embodiments portions of the catheter 120 near to the handle 110 can be constructed to have more stiffness or column strength in comparison to portions of the catheter 120 near to the cutting head 140 that can be constructed to have more compliance or flexibility.

Referring also to FIG. 2, in some embodiments the catheter 120 can be an extrusion that defines multiple lumens therein. For example, in the depicted embodiment, the catheter 120 defines at least two lumens that each slidably receive a guidewire 104*a*/104*b* therein. In the depicted embodiment, the two guidewire lumens defined within the catheter 120 distally terminate at respective locations 122*a* and 122*b* through outer diameter wall surface of the catheter 120. The respective locations 122*a* and 122*b* are located proximal of a distal end of the catheter 120. In the depicted embodiment, the first and second guidewires 104*a* and 104*b* each extend along an exterior of the catheter 120 between: (i) the respective locations 122*a* and 122*b* through the outer diameter wall surface of the catheter 120 and (ii) the cutting head 140 (including the first and second cutting head guidewire lumens of the cutting head 140). In some embodiments, the catheter 120 defines one or more additional lumens for features such as aspiration, insufflation, visualization, cauterization, medicant supply, and the like.

Figure 3:
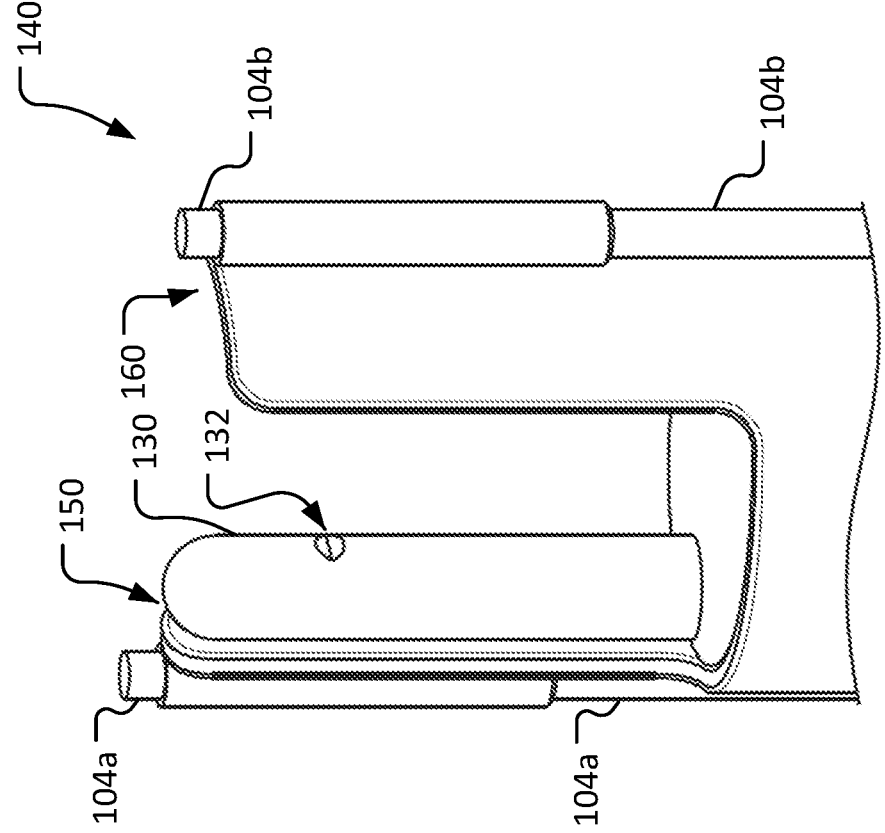
FIG. 3 is perspective view of an example cutting head that can be included in some embodiments of the intravascular cutting devices described herein.

Referring also to FIGS. 3 and 4, the catheter 120 includes and encases a hypotube 130 that defines a lumen for conveying a cutting fluid. In the depicted embodiment, the hypotube extends through an entire length of the catheter 120 and extends from a distal end of the catheter 120 into the cutting tip 140. The hypotube 130 can include one or more smooth bends along its length (e.g., see FIG. 4). While the depicted embodiment includes a single hypotube 130 for conveying cutting fluid. In some embodiments, two or more hypotubes 130 are included that can merge two or more different types of fluids/solutions that can include particulate in some cases.

The hypotube 130 can be constructed of any suitable material. For example, in some embodiments the hypotube 130 made of stainless steel, nitinol, titanium, other metallic materials, or a polymeric material, without limitation. The hypotube 130 can be scalable to any suitable size in terms of wall thickness and lumen diameter. For example, in some embodiments the hypotube 130 is an 18 TW gauge hypotube with an outer diameter of 0.05 inches (1.27 mm), an inner diameter of 0.0380 inches (0.965 mm), and a wall thickness of 0.0060 inches (0.152 mm). In another example embodiment, the hypotube 130 is a 20 RW gauge hypotube with an outer diameter of 0.0355 inches (0.902 mm), an inner diameter of 0.0235 inches (0.597 mm), and a wall thickness of 0.0060 inches (0.152 mm). The hypotube 130 can be treated to obtain a suitable stiffness/compliance and kink resistance.

The cutting head 140 is attached to and extends distally from the distal end of the catheter 120. In some embodiments, the cutting head 140 is selectively attachable and detachable from the catheter 120 such that a clinician user can select different types or sizes of cutting heads for different purposes. Alternatively, in some embodiments the cutting head 140 can be permanently affixed to the distal end of the catheter 120.

In some embodiments, the cutting head 140 is made of a hypotube that is formed to define a fluid jet prong 150 and a deflector prong 160. In particular embodiments, the cutting head 140 is made is other manners such as, but not limited to, 3D printing, over-printing, molding, over-molding, machining, laser cutting, and the like, and combinations thereof. The fluid jet prong 150 and the deflector prong 160 can be positioned on opposite sides of the cutting head's longitudinal axis 102. For example, the fluid jet prong 150 and the deflector prong 160 can be positioned (e.g., centered) at radial positions that are about 180 degrees apart from each other about the longitudinal axis 102.

In the depicted embodiment, the hypotube 130 extends into the cutting tip and becomes attached to, or a part of, the fluid jet prong 150. Accordingly, the hypotube 130 defines a cutting head lumen that conveys a cutting fluid from the catheter 120. In other words, the cutting head lumen of the fluid jet prong 150 is in fluid communication with the cutting fluid conveyance lumen of the hypotube 130 in the catheter 120. In some embodiments, the hypotube 130 is attached (e.g., by welding) to the fluid jet prong 150.

The cutting head lumen defined by the hypotube 130 in the fluid jet prong 150 distally terminates at a nozzle opening 132. The nozzle opening 132 is the location from which a fine high-pressure jet of cutting fluid is expelled out of the hypotube 130 such that it can cut a material positioned between the fluid jet prong 150 and the deflector prong 160. In the depicted embodiment, the nozzle opening 132 is a hole defined through the wall of the hypotube 130.

The deflector prong 160 blocks the high-pressure jet of cutting fluid that is expelled from the nozzle opening 132 from contacting other tissue or materials that are not intended to be cut. Hence, the deflector prong 160 acts as a backstop or anvil in relation to the jet of cutting fluid. The deflector prong 160 can be specifically designed to disperse the fluid energy of the cutting fluid expelled from the nozzle opening 132. In some embodiments, the deflector prong 160 is shaped like a concave trough that extends parallel to the cutting head axis 102.

Still referring to FIGS. 1-4, the cutting head 140 defines a first cutting head guidewire lumen 142a and a second cutting head guidewire lumen 142b within which the guidewires 104a and 104b, respectively, are slidably received. Thus, the guidewires 104a-b extend through the two guidewire lumens defined within the catheter 120, exit respective locations 122a and 122b through outer diameter wall surface of the catheter 120, extend along an exterior of the catheter 120, and then extend through the first and second cutting head guidewire lumens 142a-b. The guidewires 104a-b are placed in the patient first, and the intravascular cutting device 100 is then advanced over the guidewires 104a-b. Accordingly, the guidewires 104a-b are used to position the cutting head 140 in the desired location and orientation for cutting one or more materials as desired by a clinician user. In other words, the guidewires 104a-b can be installed on opposite sides of the material(s) to be cut, and then by virtue of the advancement of the intravascular cutting device 100 over the guidewires 104a-b the material (s) to be cut will be positioned between the fluid jet prong 150 and the deflector prong 160. The material to be cut can include, but is not limited to, soft tissue, calcified tissue, bone, fabrics, metal frames, plastics, stents, stent grafts, valves, occluders, screws, implants, and other native materials and/or implanted prosthetic materials.

In the depicted embodiment, the first cutting head guidewire lumen 142a is radially aligned with the fluid jet prong 150, and the second cutting head guidewire lumen 142b is radially aligned with the deflector prong 160. Moreover, in the depicted embodiment the first cutting head guidewire lumen 142a is radially outward of the fluid jet prong 150, and the second cutting head guidewire lumen 142b is radially outward of the deflector prong 160. In some embodiments, the first cutting head guidewire lumen 142a is not radially aligned with the fluid jet prong 150, and/or the second cutting head guidewire lumen 142b is not radially aligned with the deflector prong 160. Moreover, in some embodiments the first cutting head guidewire lumen 142a is radially inward of the fluid jet prong 150, and/or the second cutting head guidewire lumen 142b is radially inward of the deflector prong 160.

Figure 6:
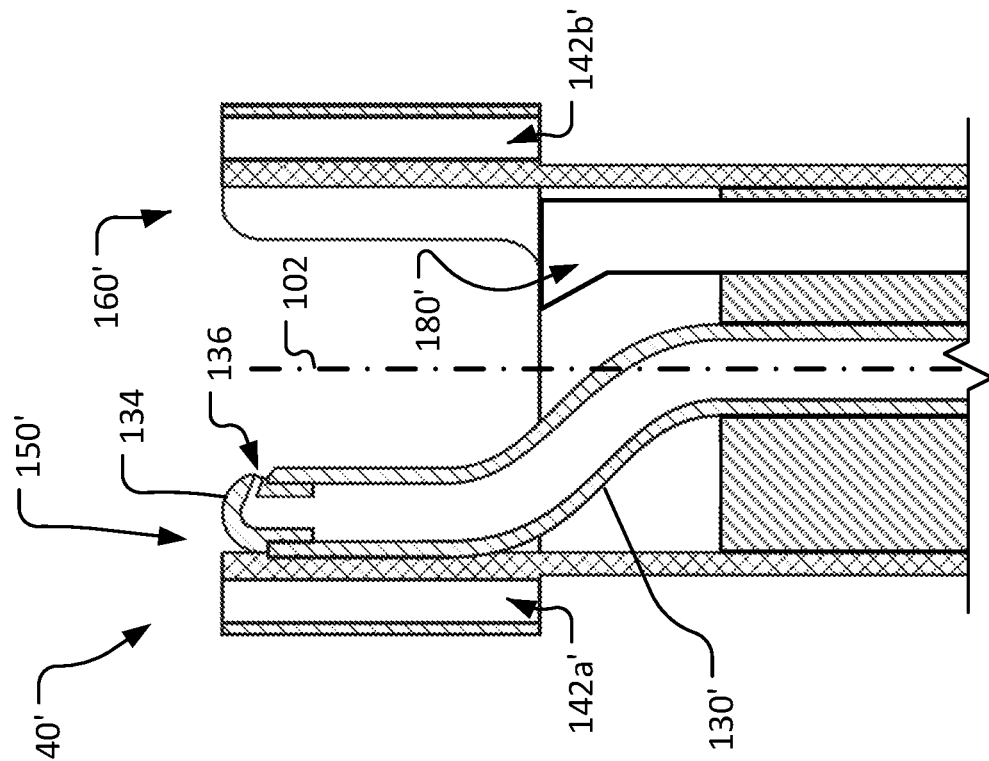
FIG. 6 is a longitudinal cross-sectional view of the cutting head of FIG. 5.
Figure 5:
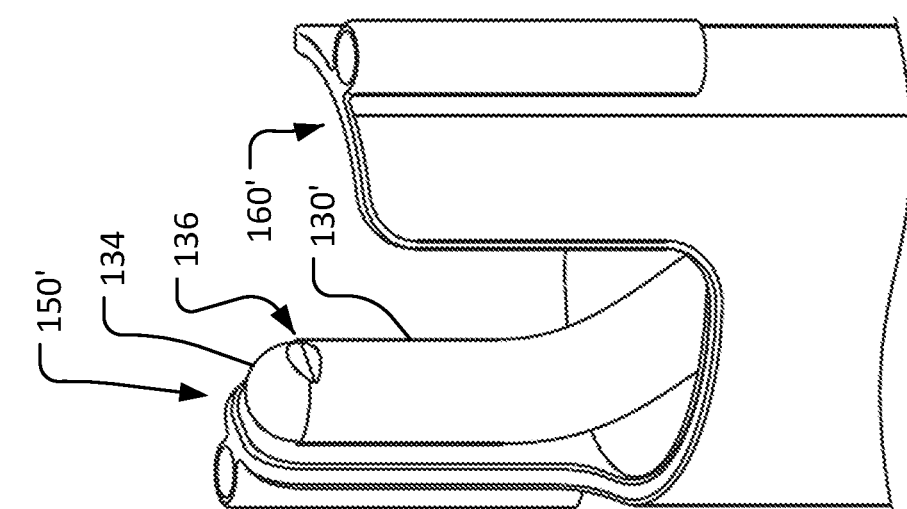
FIG. 5 is perspective view of another example cutting head that can be included in some embodiments of the intravascular cutting devices described herein.

Referring to FIGS. 5 and 6, another example embodiment of a cutting head 140' can be used as part of the intravascular cutting device 100. In this example, the cutting head 140' includes features that are analogous to the cutting head 140 described above, and such analogous features are identified by the same reference number including a prime symbol. However, the cutting head 140' is different from the cutting head 140 in that the hypotube 130' is capped by a tip 134 that defines a nozzle opening 136 that directs the high-pressure jet of cutting fluid toward the deflector prong 160'.

Referring to FIG. 7, another example embodiment of a cutting head 240 can be used as part of the intravascular cutting device 100. The cutting head 240 includes a fluid jet prong 250 and a deflector prong 260. The cutting head 240 defines a first cutting head guidewire lumen 242a, a second cutting head guidewire lumen 242b, and a nozzle opening 232.

The cutting head 240 is configured to couple with a hypotube of the catheter 120 (refer to FIGS. 1 and 2) that distally terminates proximal of the fluid jet prong 250. Accordingly, the cutting head 240 defines a hypotube receptacle 270 that receives a distal end portion of the hypotube of the catheter 120. When the distal end portion of the hypotube of the catheter 120 is positioned in the hypotube receptacle 270, the cutting fluid conveyance lumen of the hypotube is in fluid communication with a cutting head fluid conveyance lumen 230 defined within the fluid jet prong 250. The cutting head fluid conveyance lumen 230 distally terminates at the nozzle opening 232.

The cutting head 240 can be 3D printed in some embodiments. In some such embodiments, the deflector prong 260 includes a metallic insert that the fluid jet will strike against. 3D printing readily allows for reconfiguration and customization of the design of the cutting head 240. For example, FIG. 8 shows a variation that includes a different design of cutting head fluid conveyance lumen 230' and nozzle 232'.

Figure 10:
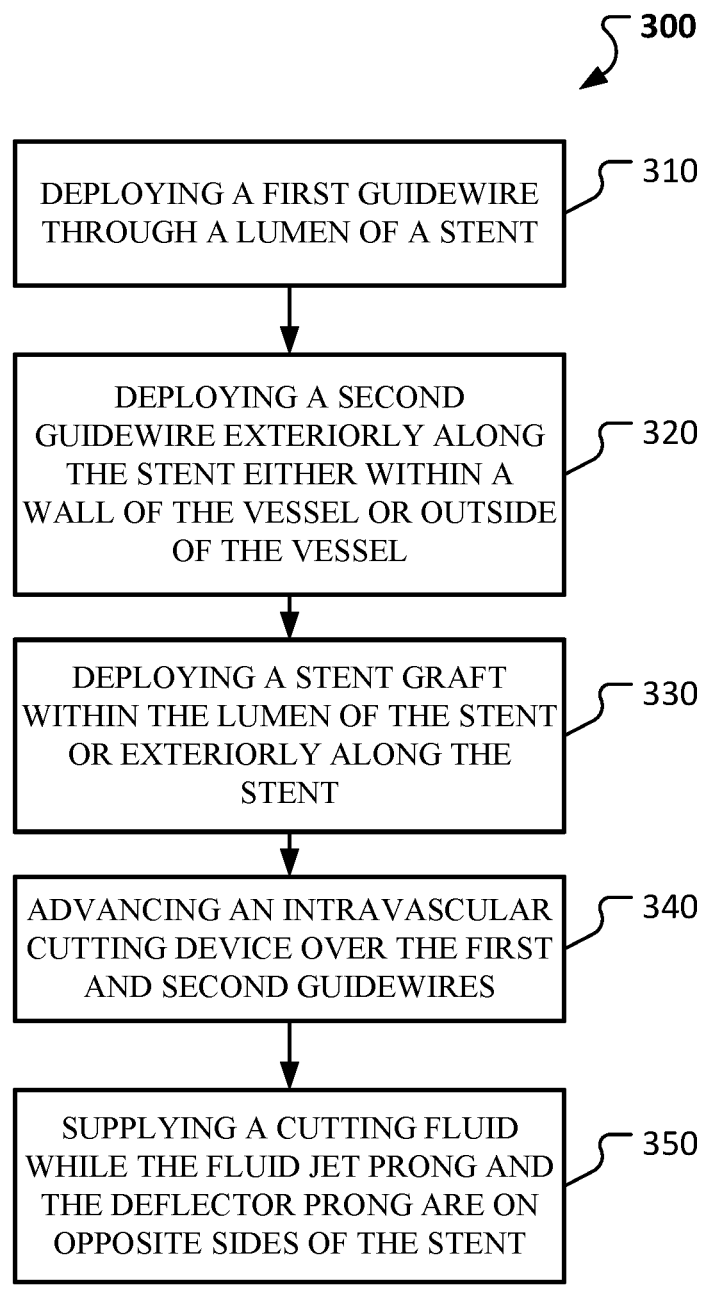
FIG. 10 is a flowchart of an example method for cutting a stent located within a vessel of a patient.
Figure 13:
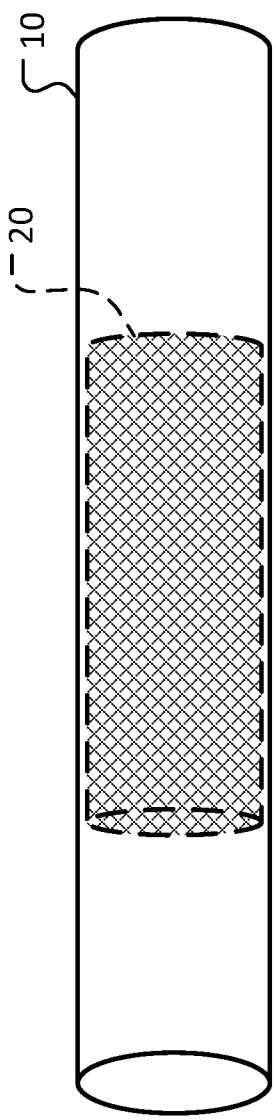
FIGS. 13-16 depict a sequence of steps of the example method of FIG. 10 for cutting a stent located within a vessel of a patient.

Referring to FIG. 10, an example method 300 can be performed using the intravascular cutting devices described herein to cut a tough material, such as a stent, located within a vessel of a patient. FIG. 13 illustrates such a stent 20 within a vessel 10. While this example method 300 pertains to the cutting of a stent, in situ, it should be understood that the method 300 can also be readily adapted to cutting other materials such as, but not limited to, stent grafts, prosthetic valves, occluders, bone screws, calcified lesions, bone, and the like.

Figure 14:
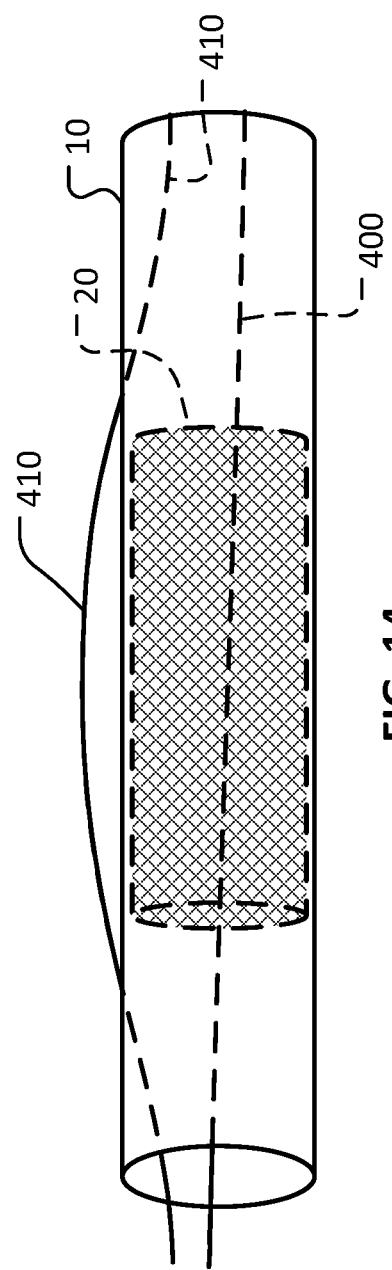

Still referring to FIG. 10, in step 310, a first guidewire is deployed through a lumen of the stent to be cut. In step 320, a second guidewire is deployed exteriorly along the stent either within a wall of the vessel or outside of the vessel. In particular, the second guidewire will be advanced through the lumen of the vessel, then either within the wall of the vessel or outside of the vessel along the location of the stent, and then back into the lumen of the vessel on the other side of the stent. This arrangement is illustrated in FIG. 14, which includes the first guidewire 400 deployed through the lumen of the stent 20 and the second guidewire 410 deployed exteriorly along the stent 20 either within the wall of the vessel 10 or outside of the vessel 10 (here the second guidewire 410 is depicted outside of the vessel 10).

Figure 15:
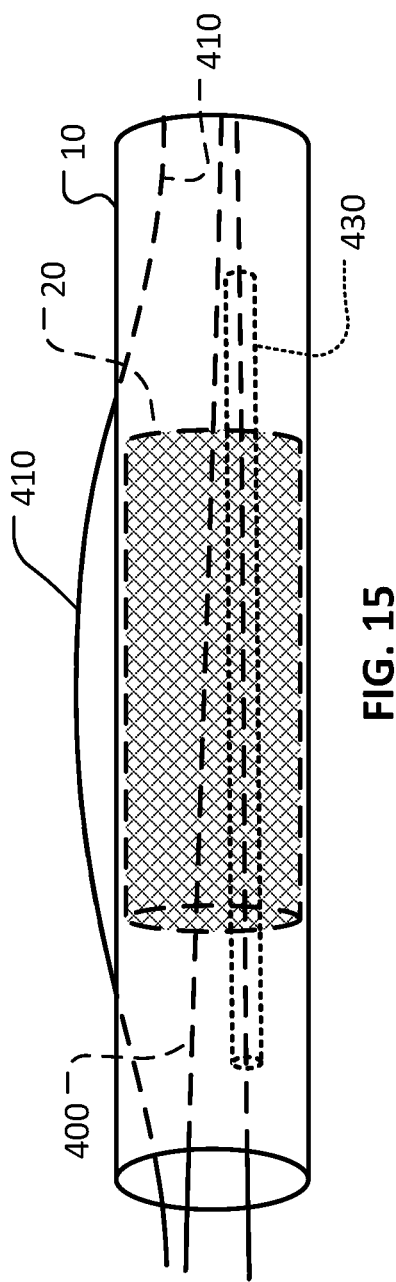
Figure 16:
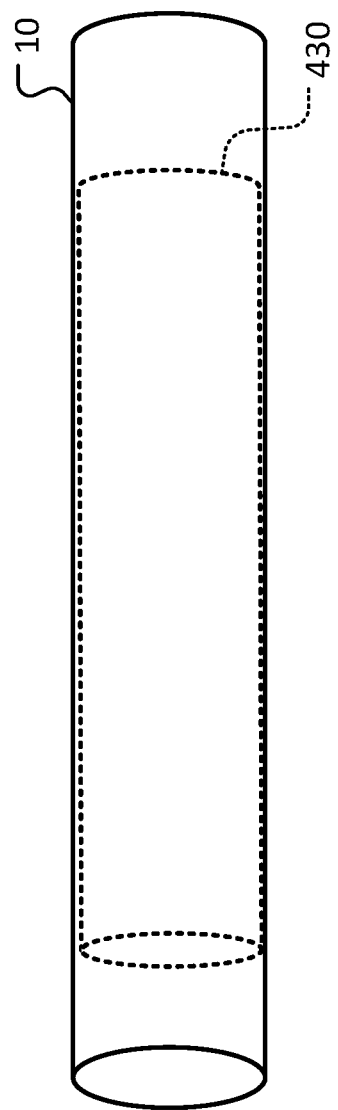

Still referring to FIG. 10, in step 330, a stent graft is deployed within the lumen of the stent or exteriorly to the stent but within the vessel. The stent graft will extend both distally and proximally beyond the length of the stent. This arrangement is illustrated in FIG. 15, which includes the stent graft 430. As depicted in FIG. 16, the stent graft 430 will be expanded to seal against the inner wall of the vessel 10 both proximally and distally of the stent 20.

Still referring to FIG. 10, in step 340, an intravascular cutting device (such as any embodiment of the intravascular cutting device 100 described herein) is advanced over the first and second guidewires. The intravascular cutting device can be configured in accordance with any of the embodiments and optional features described herein. By virtue of the placements of the first and second guidewires on opposite sides of the stent, when the intravascular cutting device is advanced over the guidewires an edge portion of the stent will be positioned between the fluid jet prong and the deflector prong of the intravascular cutting device.

In step 350, a cutting fluid is supplied into the cutting fluid conveyance lumen of the intravascular cutting device while the fluid jet prong and the deflector prong are on opposite sides of the stent. Accordingly, the cutting fluid will: (i) spray out of the nozzle opening, (ii) cut through the stent, and (iii) strike the cutting fluid deflection surface. The intravascular cutting device can be advanced along the stent while the cutting fluid is supplied. In that manner, the entire length of the stent can be cut.

During and after the cutting, the deployed stent graft serves as a prosthetic vessel lumen for the vessel (even if the wall of the vessel is cut in conjunction with the cutting of the stent). In some embodiments, the method 300 also includes aspiration of fluids and stent material particles from between the fluid jet prong and the deflector prong.

In some embodiments, in order to enhance the cutting performance of the cutting fluid, particulate can be added to the cutting fluid to increase the abrasive properties of the cutting fluid. Such particulate can be especially advantageous for cutting tough materials, such as the stent (made of metal) described in the method 300. In some embodiments, the particulate can be sodium chloride crystals, for example. The crystals/particulate can be suspended in solution and can be of the proper size to be expelled through the nozzle opening of the cutting head.

In some such embodiments, crystals or other types of particulate can be added directly to the source of cutting fluid that is then pumped through the intravascular cutting device. In other embodiments, the crystals or other types of particulate can be in a separate solution that is mixed with the primary source of cutting fluid at a point within the intravascular cutting device. In such a case, the catheter of the intravascular cutting device can include a first hypotube for conveying the primary cutting fluid and a second hypotube for conveying the solution containing the crystals or other types of particulate. The two hypotubes can each be confluent with and in fluid communication with the cutting head lumen.

In some embodiments, the two hypotubes conjoin such that the fluids can mix in a ratio that is selectively adjustable. In some such embodiments, a valve such as an adjustable needle valve is used to adjustably-mix the primary cutting fluid and the solution containing the crystals or other types of particulate.

Figure 11:
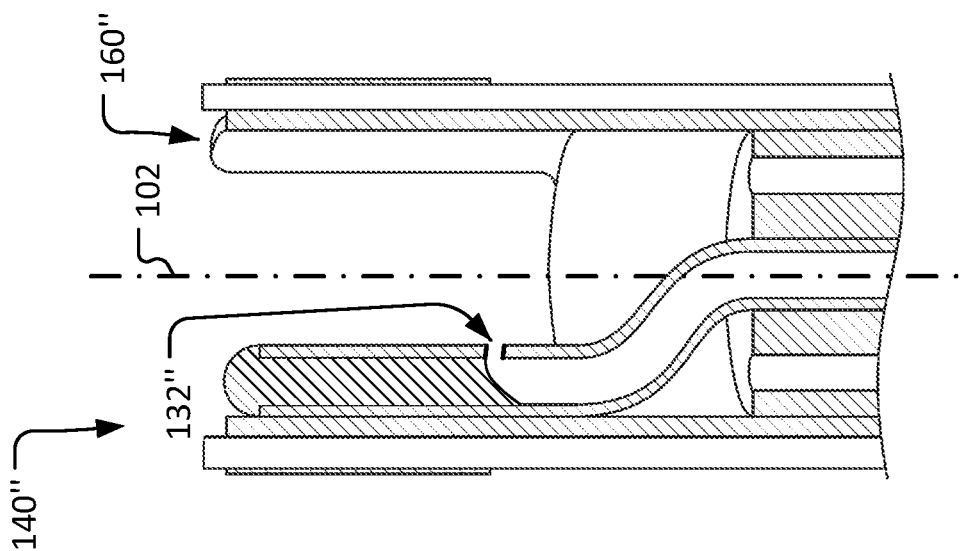
FIG. 11 is a perspective longitudinal cross-sectional view of another example cutting head that can be included in some embodiments of the intravascular cutting devices described herein.

Referring to FIG. 11, another example cutting head 140" can be used as part of the intravascular cutting device 100 (FIG. 1). In this example, the cutting head 140" includes features that are analogous to the cutting head 140 described above (refer to FIG. 4). However, the cutting head 140" is different from the cutting head 140 in that the nozzle opening 132" that directs the high-pressure jet of cutting fluid toward the deflector prong 160" is positioned more proximally than the nozzle opening 132 of the cutting head 140. In the depicted embodiment, the nozzle opening 132" directs the high-pressure jet of cutting fluid toward the deflector prong 160" at a location on the deflector prong 160" that is proximal of the middle of the deflector prong 160".

Figure 12:
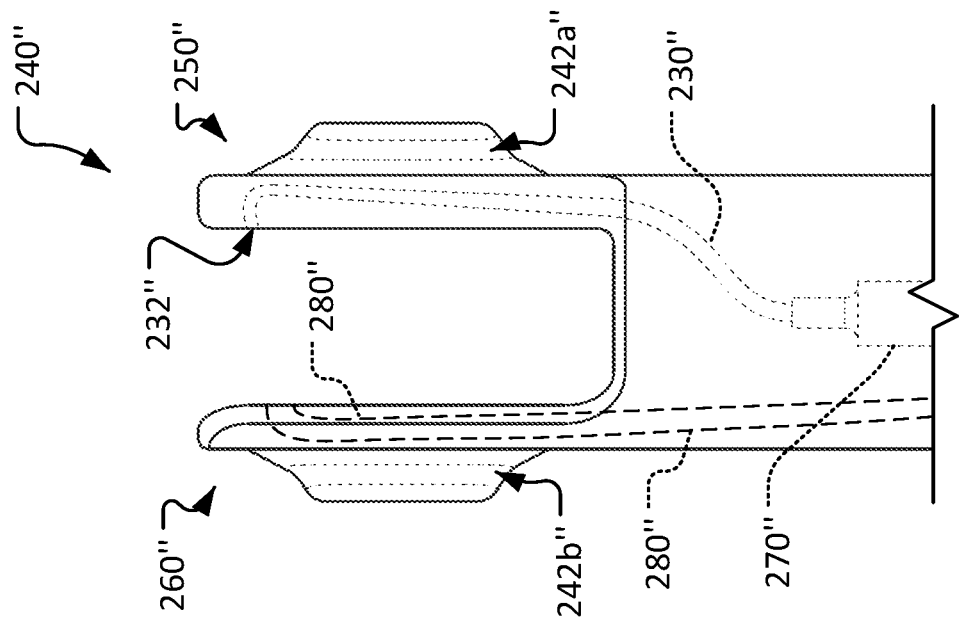
FIG. 12 is a side view of another example cutting head that can be included in some embodiments of the intravascular cutting devices described herein.

Referring to FIG. 12, another example cutting head 240" can be used as part of the intravascular cutting device 100 (FIG. 1). In this example, the cutting head 240" includes features that are analogous to the cutting head 240' described above (refer to FIG. 8). However, the cutting head 240" is different from the cutting head 240' in that it includes an aspiration port and lumen 280" defined within the deflector prong 260". Alternatively or additionally, an aspiration port and lumen can be defined within the fluid jet prong 250".

Additional Optional Features

In some embodiments, the cutting head and/or the catheter of the intravascular cutting devices described herein are configured to facilitate aspiration of fluids and/or particles from between the fluid jet prong and the deflector prong. For example, as shown in FIG. 6, an aspiration port and lumen 180' can be positioned between the fluid jet prong 150' and the deflector prong 160'. In some such embodiments, the aspiration port and lumen 180' is positioned at the base of the deflector prong 160'. Other arrangements of aspiration ports and lumens are described in reference to FIG. 12.

Figure 17:
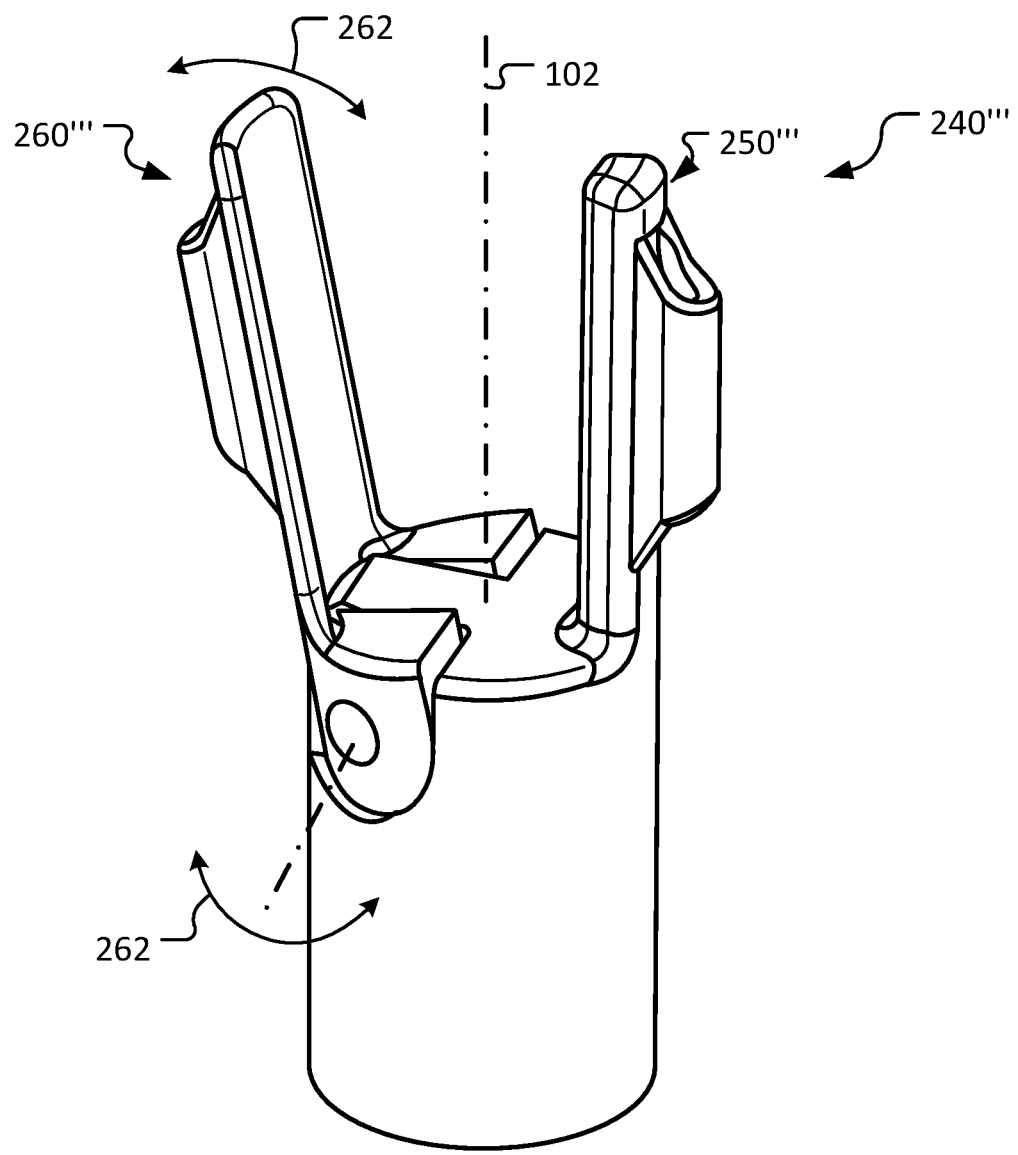
FIG. 17 is perspective view of another example cutting head that can be included in some embodiments of the intravascular cutting devices described herein.

Referring to FIG. 17, in some embodiments of the intravascular cutting devices described herein, the cutting head 240''' includes a deflector prong 260''' that is pivotable (e.g., hinged) in relation to the fluid jet prong 250''' such that a separation distance between respective distal ends of the fluid jet prong 250' and the deflector prong 260''' is variable. In some such cases, the deflector prong 260''' is selectively pivotable in relation to the fluid jet prong 250''' such that a separation distance between respective distal ends of the fluid jet prong 250''' and the deflector prong 260''' is controllably variable by a clinician user. In other words, in some embodiments the deflector prong 260''' can pivot radially toward and/or radially away from the central longitudinal axis 102 of the cutting head 240''' (e.g., as also depicted by arrows 262 of FIGS. 7 and 17). In some such cases, the deflector prong 260' is pivotable while also being spring biased toward an orientation in which it is parallel with the longitudinal axis 102 of the cutting head 240'''.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An intravascular cutting device, comprising:
   a catheter defining a first guidewire lumen and a second guidewire lumen, the catheter comprising a cutting fluid conveyance lumen; and
   a cutting head extending distally from the distal end of the catheter, the cutting head comprising:
      a fluid jet prong defining a cutting head lumen in fluid communication with the cutting fluid conveyance lumen, the cutting head lumen distally terminating at a nozzle opening; and
      a deflector prong defining a cutting fluid deflection surface facing toward the nozzle opening such that cutting fluid emitted from the nozzle opening strikes the cutting fluid deflection surface.

2. The intravascular cutting device of claim 1, wherein the cutting head is selectively attachable and detachable from the catheter by a user of the intravascular cutting device.

3. The intravascular cutting device of claim 2, wherein the cutting head is a first cutting head, and the intravascular cutting device further comprises a second cutting head that is selectively attachable and detachable from the catheter by a user of the intravascular cutting device.

4. The intravascular cutting device of claim 1, wherein the cutting head defines a first cutting head guidewire lumen and a second cutting head guidewire lumen.

5. The intravascular cutting device of claim 4, wherein the first cutting head guidewire lumen is radially aligned with the fluid jet prong and the second cutting head guidewire lumen is radially aligned with the deflector prong.

6. The intravascular cutting device of claim 5, wherein the first cutting head guidewire lumen is radially outward of the fluid jet prong and the second cutting head guidewire lumen is radially outward of the deflector pong.

7. The intravascular cutting device of claim 1, wherein the catheter comprises a hypotube defining the cutting fluid conveyance lumen.

8. The intravascular cutting device of claim 7, wherein the fluid jet prong comprises the hypotube such that the cutting head lumen is defined by the hypotube.

9. The intravascular cutting device of claim 7, wherein the hypotube distally terminates proximal of the fluid jet prong.

10. The intravascular cutting device of claim 7, wherein the hypotube is a first hypotube and the cutting fluid conveyance lumen is a first cutting fluid conveyance lumen, and wherein the catheter further comprises a second hypotube defining a second cutting fluid conveyance lumen, and wherein both of the first and second cutting fluid conveyance lumens are in fluid communication with the cutting head lumen.

11. The intravascular cutting device of claim 10, further comprising a valve arranged for selectively adjusting a mix ratio of fluids in the first and second cutting fluid conveyance lumens.

12. The intravascular cutting device of claim 1, wherein the cutting head defines an aspiration lumen that distally terminates between the fluid jet prong and the deflector prong.

13. The intravascular cutting device of claim 1, wherein the fluid jet prong is pivotable in relation to the deflector prong such that a separation distance between respective distal ends of the fluid jet prong and the deflector prong is variable.

14. The intravascular cutting device of claim 1, wherein the deflector prong is pivotable in relation to the fluid jet prong such that a separation distance between respective distal ends of the fluid jet prong and the deflector prong is variable.

15. The intravascular cutting device of claim 1, further comprising a handle, wherein the catheter extends distally extends distally from the handle.

16. The intravascular cutting device of claim 15, wherein the handle comprises an actuator operable to control a flow of cutting fluid to the cutting head.

17. The intravascular cutting device of claim 15, wherein the handle comprises an actuator operable to control a flow of suction for aspiration at the cutting head.

18. The intravascular cutting device of claim 15, wherein the handle comprises one or more controls operable to selectively deflect one or more portions of the catheter.

19. The intravascular cutting device of claim 1, wherein the first and second guidewire lumens extend along the catheter and distally terminate at respective locations through a wall surface of the catheter.

20. The intravascular cutting device of claim 19, wherein the respective locations are proximal of a distal end of the catheter.

* * * * *

UNITED STATES PATENT AND TRADEMARK OFFICE
CERTIFICATE OF CORRECTION

PATENT NO. : 12,178,465 B2
APPLICATION NO. : 18/379748
DATED : December 31, 2024
INVENTOR(S) : Jason N. MacTaggart, Alexey Kamenskiy and Paul Deegan Page 1 of 1

It is certified that error appears in the above-identified patent and that said Letters Patent is hereby corrected as shown below:

In the Claims

In Column 13, Line 56, In Claim 6, delete "pong." and insert -- prong. --.

In Column 14, Line 38-39 (Approx.), In Claim 15, delete "extends distally extends distally" and insert -- extends distally --.

Signed and Sealed this
Twenty-fifth Day of February, 2025

Coke Morgan Stewart
*Acting Director of the United States Patent and Trademark Office*